(12) United States Patent
Lai et al.

(10) Patent No.: US 6,610,049 B2
(45) Date of Patent: Aug. 26, 2003

(54) CUSTOMIZED LASER ABLATION OF CORNEAS WITH SOLID STATE LASERS

(75) Inventors: Ming Lai, Dublin, CA (US); Meijuan Yuan, Dublin, CA (US)

(73) Assignee: Katana Technologies GmbH, Kleinmachnow (DE)

( * ) Notice: Subject to any disclaimer, the term of this patent is extended or adjusted under 35 U.S.C. 154(b) by 34 days.

(21) Appl. No.: 09/800,084

(22) Filed: Mar. 5, 2001

(65) Prior Publication Data

US 2002/0013575 A1 Jan. 31, 2002

Related U.S. Application Data

(60) Provisional application No. 60/186,953, filed on Mar. 4, 2000.

(51) Int. Cl.[7] ............................................... A61B 18/18
(52) U.S. Cl. ............................... 606/5; 606/12; 606/166
(58) Field of Search ............................... 606/5–12, 166, 606/167

(56) References Cited

U.S. PATENT DOCUMENTS

| | | | | |
|---|---|---|---|---|
| 5,480,396 A | * | 1/1996 | Simon et al. | 606/4 |
| 5,520,679 A | | 5/1996 | Lin | |
| 6,142,989 A | * | 11/2000 | O'Donnell, Jr. | 606/5 |
| 6,210,401 B1 | | 4/2001 | Lai | |
| 6,280,435 B1 | * | 8/2001 | Odrich et al. | 606/5 |
| 6,296,649 B1 | * | 10/2001 | Hellenkamp | 606/166 |
| 6,406,473 B1 | * | 6/2002 | Shimmick et al. | 606/5 |

* cited by examiner

*Primary Examiner*—Hieu T. Vo
*Assistant Examiner*—Johnny H. Hoang
(74) *Attorney, Agent, or Firm*—Fish & Richardson P.C.

(57) ABSTRACT

A surgical laser system is described for customized ablation with a power stabilized, near diffraction-limited laser beam. This surgical laser beam has a pulse repetition rate of from near 500 Hz to about 1 kHz and has a relatively small spot size at both positions of the cornea and the scanner. Such a surgical laser beam enables the use of fast scanner and the implement of fast eye tracker. One embodiment of such a surgical laser source is a CW pumped solid state laser employing non-linear wavelength conversion.

20 Claims, 2 Drawing Sheets

CUSTOMIZED LASER ABLATION OF CORNEAS WITH SOLID STATE LASERS

This application claims the benefit of U.S. Provisional Application No. 60/186,953, filed on Mar. 4, 2000.

BACKGROUND

This application relates to methods and systems for customized cornea ablation in photo-refractive surgery.

Laser ablation can be used to remove small portions of the cornea in an eye to form a desired surface shape to improve the vision. A custom-ablation photo-refractive surgery, for example, can control a surgical laser beam by using measurements of the topographical profile of the cornea or the wavefront aberration of the eye to generate a customized ablation profile with high surgical accuracy. Such technique can be used to generate fine customized corneal profile to correct low-order refractive errors such as defocusing and astigmatism and high-order refractive errors such as coma and spherical aberrations. In comparison, conventional photo-refractive surgeries correct only the lower-order errors and may induce extra amount of high-order errors and lead to imperfections such as halo and night vision.

A widely-used laser source for the above custom-ablation photo-refractive surgery is an excimer gas laser. The output laser beam is focused onto the cornea and is scanned by a computer-controlled scanner.

SUMMARY

The techniques and systems of this application are based in part on the recognition of special needs for the custom ablation in photo-refractive surgery and in part on the recognition of certain intrinsic limitations of typical excimer lasers for the accuracy re application. For example, it is desirable in the custom-ablation procedure to precisely control the laser energy deposition on the cornea with a fast and accurate compensation for the eye movement. A laser surgical system for the custom-ablation photo-refractive surgery is proposed herein to use a solid-state laser to produce a high pulse rate and near diffraction-limited laser beam to meet the special needs of the custom ablation in photo-refractive surgery.

In one embodiment, the solid-state laser is optically pumped by a continuous-wave diode laser to produce laser pulses, and a frequency-conversion element is used to convert the laser frequency in the deep UV range near 210 nm. The pulse repetition rate is about 500 to 1200 Hz. The output pulse energy of each pulse—is about 0.25 to 0.08 mJ. The spot size of the laser beam is focused to about 0.3 to 0.6 mm on the cornea, and is 3 mm or smaller on the scanner mirror. The pulse duration is 10 ns or shorter. The pulse to pulse fluctuation of this laser source is smaller than 10%, and the quality of the ablation beam is near diffraction limit (i.e. the $M^2$ is 10 or smaller).

The fast scanner may include a pair of mirrors respectively engaged to two galvanometers and operate at a response frequency up to 1 kHz. Each of the galvanometer has a scanner mirror for a beam aperture of 5 mm or smaller. The near diffraction limited surgical laser beam enables the use of the small mirror and the fast operation of the scanner. The fast eye-tracking device may have a detection rate of kilohertz and can be coupled to the fast scanner. The near diffraction limited surgical laser beam enables the operation of the fast scanner and thus the operation of the fast eye tracker. The surgical laser system can then compensate the eye movement up to a kilohertz.

With a near diffraction-limited beam quality, this solid state laser allows for the use of the small scanner mirror for achieving fast scanning and engaging fast eye tracking.

DETAILED DESCRIPTION

Figure 1:
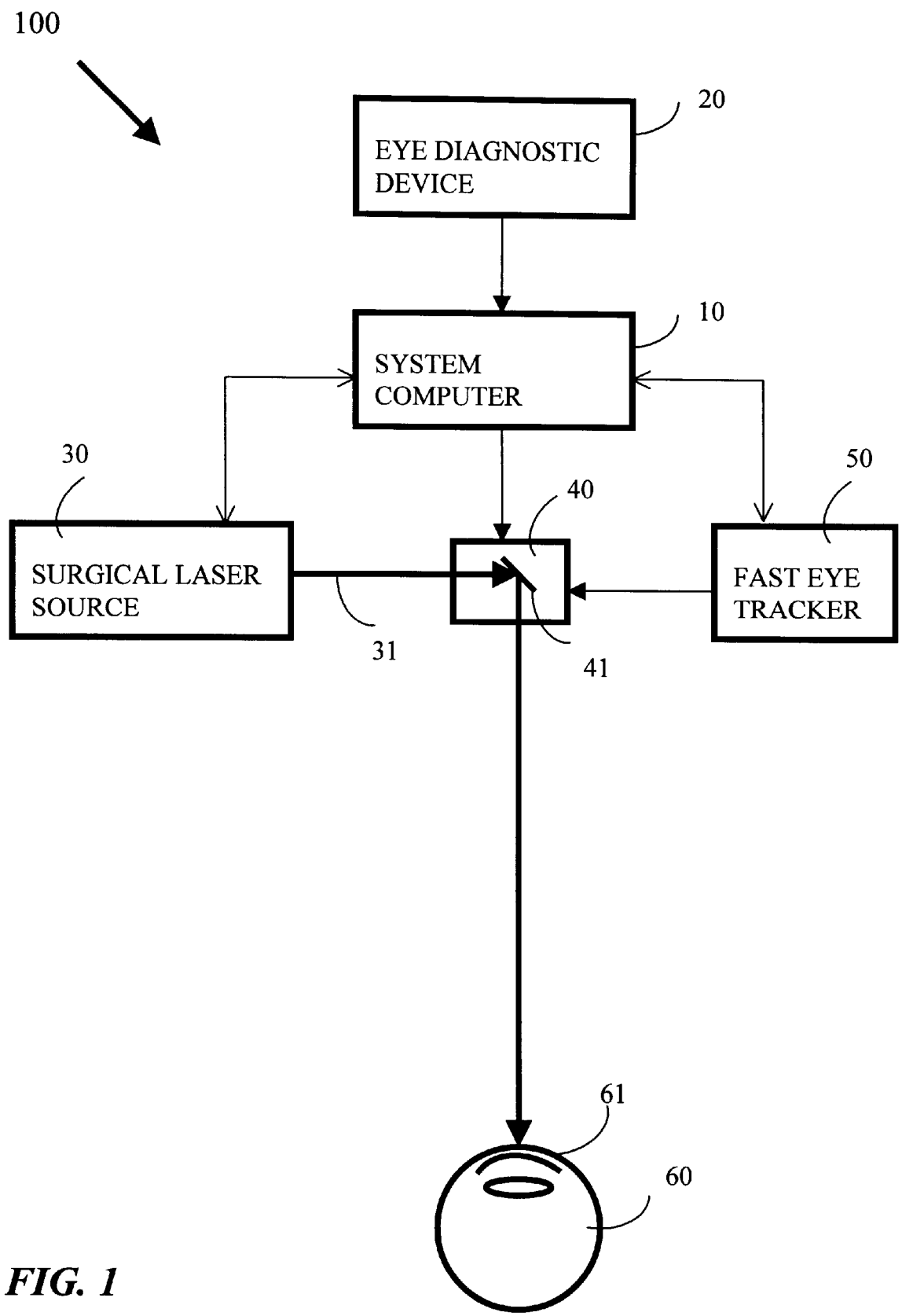
FIG. 1 shows schematically an eye surgical system for custom ablation in the photo-refractive surgery in accordance with one embodiment.

FIG. 1 shows one embodiment of a laser surgical system 100 for custom ablation in photo-refractive surgery. The system 100 includes a control unit 10, an eye diagnostic device 20, a surgical laser source 30, a fast scanner 40, and a fast eye-tracking device 50. The control unit 10 may include a computer processor or a computer for controlling the system operation. The eye diagnostic device 20 is operable to independently measure the topographical profile of the cornea 61 and/or the refractive error of the eye 60. This diagnostic device 20 may be implemented by a wavefront device or corneal tomography device. The laser source 30 is a solid-state laser operable to produce a surgical laser beam 31 with specified pulse and beam properties for the custom ablation. The fast scanner 40, having at least one scanner mirror 41, is operable to direct and scan the laser beam 31 through the free space on the cornea 61 of an eye 60 at a high speed for the custom ablation. The eye-tracking device 50 is used to track the movement of the eye 60 during the surgery and to inform the control unit 10 of such eye movement.

In operation, the eye diagnostic device 20 is first operated to measure the refractive errors or corneal irregularities of the eye 60. The measurement data is fed into the control unit 10 to generate a customized ablation profile based on a selected program algorithm. One example of the program algorithm is described in U.S. Pat. No. 5,949,521 to Williams and Liang. During the surgery, the control unit 10 controls the fast scanner 40 to deposit laser energy from the laser source 30 onto the cornea 61 to produce a customized laser ablation profile. The fast eye tracker 50 detects the instantaneous eye position and the detected signal of eye displacement is used to offset the fast scanner 40 such that the surgical laser beam 31 can follow the movement of the eye 60 during the surgery.

The system 100 may be generally configured to produce a beam spot on the cornea 61 as small as possible to achieve a fine lateral spatial ablation resolution along the corneal surface. The pulse energy of each pulse should also be sufficiently small to produce a small ablation depth to achieve a high spatial resolution perpendicular to the corneal surface. Each surgical location on the cornea 61 receives many pulses during the surgery by scanning the beam 31 along a pre-determined scanning pattern. The pulse energy should be consistent from pulse to pulse so that the ablation depth is substantially a constant to produce a predictable and smooth surface profile to match the pre-selected custom surface profile. Hence, The pulse repetition rate of the laser 30 should be sufficiently high and the pulse width should be sufficiently short.

The above desired conditions impose further conditions on the system 100. For example, the scanning speed of the scanner 40 should also be fast to achieve at least two effects. First, the spatial locations of two adjacent pulses should be sufficiently separate apart along the scanning path to reduce the adverse impact of the scattered particles produced by the first pulse on the subsequent, second pulse since such scattered particles can reduce the actual energy of the subsequent pulse that reaches the cornea 61. Second, the fast scanning can eliminate the spatial overlap of two adjacent pulses on the cornea 61 and hence avoids over ablation at a particular location.

The fast scanning, in turn, requires the scanning mirror 41 to be light in order to reduce the inertia for moving the mirror 41. Therefore, the surface area of the mirror 41 should be small. This condition requires the beam size at the scanning mirror 41 to be small. Notably, a beam-shaping optical element such as a lens or a lens combination is not placed in the optical path between the scanner mirror 41 and the eye 60 so that the beam 31 can be accurately controlled by the scanning mirror 41. Therefore, the beam 31 incident to the scanning mirror 41 should be nearly diffraction limited so that the beam size can be small at both the mirror 41 and the eye 60.

This condition further requires that the laser beam 31 should be a high-quality beam at the output of the laser 30. Assuming the output beam of the laser 30 were a low-quality beam, it is generally difficult to maintain a small beam size over a distance since the poor beam quality causes the beam to be highly divergent. A proper lens or lens combination may be used between the laser 30 and the scanner 40 to focus such a beam to a small spot size at a particular location, e.g., on the cornea 61 of the eye 60. But since the beam quickly diverges, the beam size at a location spaced away from the focused spot can be large. Hence, the actual beam size at the scanning mirror 41 may be too big to make the scanner to scan at the desired high scanning speed. As the result, the poor beam quality of the output laser beam 31 from the laser 30 not only adversely affects the lateral spatial ablation resolution but also reduces the spatial ablation resolution in the direction perpendicular to the corneal surface.

The above recognition suggests that, when a typical commercial excimer laser is used as the laser 30 in the system 100, the ablation performance of the system 100 is limited by the intrinsic characteristics of the excimer laser. For example, one limitation of many commercial excimer lasers is a large pulse-to-pulse energy fluctuation. A fluctuation of 20% or more can be common for typical commercial excimer lasers used in refractive laser surgery systems. This fluctuation can significantly degrade the otherwise achievable accuracy of energy deposition on the cornea 61.

As another example, typical excimer lasers generally have a low repetition rate of pulse generation. A pulse repetition rate of 100 Hz or lower is typically used for refractive surgery. Higher repetition rate usually leads to bigger pulse-to-pulse fluctuation and degrades laser performance. This low repetition rate limits the beam spot size to about 1 mm on the cornea 61 and thus limit the fineness, the spatial resolutions along directions perpendicular and laterally along the corneal surface, of the final ablation profile.

In addition, many commercial excimer lasers have poor beam quality. A typical commercial excimer may have a rectangular beam profile, and the intensity distribution varies across the beam and changes with the age of laser optics and discharge electrodes. Usually, the beam collimation is poor and thus is highly divergent. As a result, the beam spot size on the scanner 40 is typically large. The scanner mirror 41, thus, need be large to direct the beam 31 without loss due to beam clipping. The speed of the scanner 40 is generally limited by the rotation inertia of the mirror 41 and, consequently, poor beam quality of the excimer laser limits the speed of the scanner 40. Such a slow scanner can prohibit precise disposition of pulses at high repetition rate and forbid fast response of eye tracking.

It is further recognized that, a solid-state laser, when properly configured, can overcome the intrinsic limitations of the excimer laser and meet the laser requirements of the system 100 for the customized cornea ablation in photo-refractive surgery. For example, such a solid-state laser may be operable to produce a beam with good beam quality which has a beam spot size less than 3 mm on the scanning mirror 41 and about 300 to 600 microns on the cornea 61 that is spaced about 25 to 30 cm away from the scanner 40. This working distance is about 25 to 30 cm between the scanner mirror 41 and the cornea 61 and is greatly desirable for photo-refractive surgeries. The power fluctuation of the surgical laser beam 31 can be less than 10% by using such a solid-state laser with a repetition rate of about 400–1200 Hz. Such beam characteristics are generally difficult to achieve in many commercial excimer lasers.

It is advantageous for the surgical laser beam 31 to have a pulse energy fluctuation smaller than 10% in the customized ablation. For instance, an UV laser beam with an energy density of about 125 mJ/cm2 is commonly used to achieve an ablation depth of about 0.25-micron per pulse. Such a fine ablation depth is desirable for obtaining a fine ablation profile. The energy density used is only about twice as much as the threshold energy density for ablating corneal tissue. Therefore, a typical 20% pulse energy fluctuation of excimer lasers induces an approximate 40% fluctuation in ablation depth from pulse to pulse. Reducing the pulse energy fluctuation to 10% or better can significantly improve the smoothness of the ablated surface and thus the precision of the laser surgery.

The spot size of about 300 to 600 microns on the cornea 61 can be shown as a preferable range for generating fine ablation profile in the custom cornea ablation. Typically, an optical zone of about 6 mm is ablated on the cornea for refractive correction. To obtain fine ablation features in custom cornea ablation, laser beam spot of one tenth of the zone size or smaller is generally desirable. The pulse energy density should be approximately unchanged as the beam spot size is reduced. For instance, to maintain a typical energy density of 125 mJ/cm2 for UV ablation, the optimal pulse energy is thus about 0.1 (for a 300 micron spot size) to 0.5 mJ (for a 600 micron spot size).

The pulse repetition rate of about 400 to 1200 Hz becomes necessary in order to complete the custom ablation surgery in a comparable amount of time of the conventional refractive surgery. The surgical time is proportional to the square of beam spot size and reversibly proportional to the pulse repetition rate, provided the pulse energy density is kept constant. A significant higher repetition rate is desirable for custom ablation in comparison to conventional refractive surgery. On the other hand, a pulse repetition rate much higher than 1 kHz may not practical because this may reach the practical limit in the response time for commercial scanners.

Figure 2:
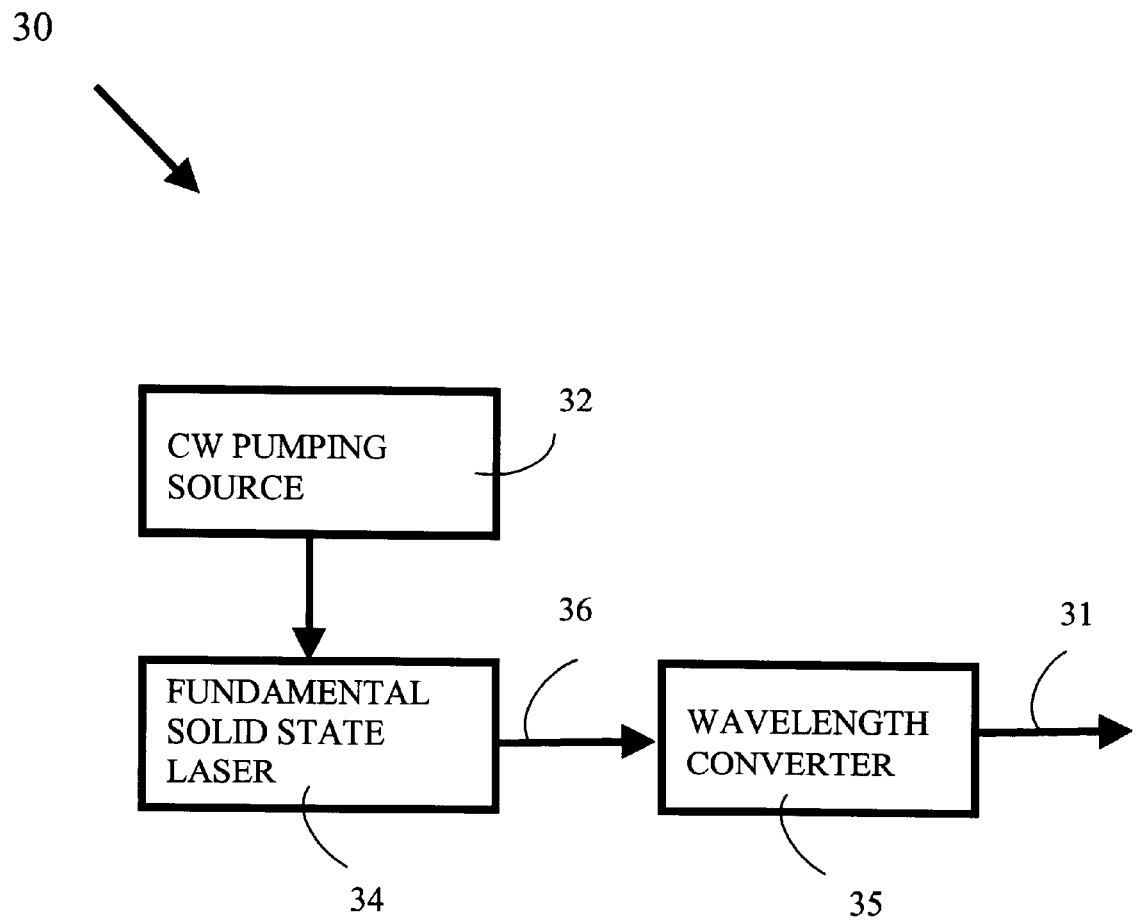
FIG. 2 illustrates one implementation of the solid state laser in the system in FIG. 1.

FIG. 2 shows a block diagram of one embodiment of a solid-state laser as the surgical laser source 30. A continuous-wave optical pumping source 32 is used to pump a fundamental solid-state laser 34. This fundamental solid-state laser 34 produces a pulsed laser beam 36 with a repetition rate of about 400–1200 Hz, a near diffraction-limited beam quality, a pulse duration of 10 ns or shorter, and a pulse to pulse fluctuation less than a few percent. The output beam of the laser 34 is then converted to a surgical laser beam 31 by a nonlinear optical wavelength converter 35.

The laser in FIG. 2 may be implemented in a number of configurations. For example, the surgical laser source 30 may use a diode-pumped, cascaded Ti:sapphire laser, as disclosed in U.S. Pat. No. 6,031,854 to Ming Lai. In that laser source, a CW diode laser array pumps a Nd:YLF, Nd:YAG, or Yb:YAG laser; This first solid state laser is Q-switched, frequency-doubled in an intracavity nonlinear medium to produce a green laser at about 530 nm and about 0.5 to 1 kHz. The green laser beam is then used to pump a gain-switched Ti:sapphire laser to produce a fundamental solid state laser of stable pulse energy and near diffraction limited beam quality. This fundamental solid state laser is tuned to a wavelength about 840 nm. A wavelength converter converts the laser beam at 840 nm to a laser beam at about 210 nm through the fourth harmonic generation. This 210-nm UV laser can then service as a surgical laser beam 31 in FIG. 1.

In another configuration, the surgical laser source 30 may include a diode pumped, Q-switched Nd:YLF, Nd:YAG, or Yb:YAG laser, producing a UV laser beam. In this laser source, a diode laser array pumps a Nd:YLF, Nd:YAG, or Yb:YAG laser to produce a fundamental laser at a wavelength of about 1 micron. This fundamental laser is Q-switched at about 0.5 to 1 kHz to produce stable pulse energy and near diffraction limited beam quality. This fundamental solid state laser is then converted to about 210 nm by the fifth harmonic generation. This 210-nm UV laser beam can then service as a surgical laser beam 31 of FIG. 1.

As a third exemplary configuration, the surgical laser source 30 may include a diode pumped, Q-Switched Nd:YLF, Nd:YAG, or Yb:YAG laser, producing a mid-infrared laser beam. In this laser source, a CW diode laser array pumps a Nd:YLF, Nd:YAG, or Yb:YAG laser to produce a fundamental laser at a wavelength of about 1 micron. This fundamental laser is Q-switched at about 0.5 to 1 kHz to produce stable pulse energy and near diffraction limited beam quality. An optical parametric oscillator may be used to convert the laser output of this fundamental solid state laser into a laser beam at a wavelength in the mid-infrared range near 3 micron. This 3-micron laser beam can then service as a surgical laser beam 31 of FIG. 1.

Referring back to FIG. 1, the surgical laser-beam 31 of about 3 mm or smaller on the scanner mirror 41 allows for the use of a small scanner mirror 41 (e.g., for an optical aperture of about 5 mm). This small scanner mirror 41 in turn enables the operation of a fast scanner 40. The fast scanner 40 may include a pair of mirror engaged to two galvanometers that scan the mirrors in orthogonal directions, respectively. The fast scanner 40 can have a response rate of 500 Hz or higher (e.g., 1200 Hz). One example of such a fast scanner 40 is Galvanometer G120, manufactured by General Scanning of Watertown, Mass.

The fast scanner 40 in turn enables the implement of the fast eye tracker 50. The fast eye tracker 50 can have a detection rate of 500 Hz or higher. With the operation of the fast scanner 40, the surgical laser system 100 can then have a response rate of about 500 Hz or higher to the eye movement. Such a response rate is required to compensate for involuntary eye movement. Examples of fast eye trackers are described in U.S. Pat. No. 6,179,422 to Lai and in WO 00/04952 published on Jul. 20, 1999 (WIPO).

The fast scanner 40 and fast eye tracker 50 have also made it possible to dispose precisely surgical laser beam 31 of high pulsed rate. It is well known in the art that uniform pulse energy disposition may be disturbed by plume from laser ablation. Fast scanning and big separation between consecutive pulses are effective scheme to minimize the plume disturbance. An example to achieve fast scanning and big separation between consecutive pulses is described in WO 00/10037 published on Feb. 24, 2000.

Although the present disclosure only includes a few embodiments, other modifications and enhancements may be made without departing from the following claims.

What is claimed is:

1. A surgical laser system for customized corneal ablation of a cornea of an eye, comprising:

an eye diagnostic device operable to measure a cornea or refractive defect of the eye;

a solid-state laser operable to produce a pulsed ablation laser beam at a predetermined wavelength, wherein said ablation laser beam is power stabilized and near diffraction- limited;

an optical scanner positioned to receive and scan said ablation laser beam on the cornea of the eye;

an eye-tracking device operable to detect movement of the eye; and a control unit coupled to communicate with said eye diagnostic device, said solid-state laser, said optical scanner, and said eye-tracking device, and operable to control said scanner to produce a customized laser-ablation profile on the cornea for correcting the defect of the eye and to offset said scanner to compensate for any eye movement according to a signal from said eye-tracking device.

2. The system as in claim 1, wherein said eye diagnostic device includes a wavefront device to measure refractive error and aberration of the eye.

3. The system as in claim 1, wherein said eye diagnostic device includes a corneal tomography to measure cornea irregularity.

4. The system as in claim 1, wherein said solid-state laser comprises a CW optical pumping source, a fundamental solid-state laser, and a wavelength converter.

5. A surgical laser system for customized corneal ablation of a cornea of an eye, comprising:

an eye diagnostic device operable to measure a cornea or refractive defect of the eye;

a solid-state laser operable to produce a pulsed ablation laser beam at a predetermined wavelength, wherein said ablation laser beam is power stabilized and near diffraction- limited;

an optical scanner positioned to receive and scan said ablation laser beam on the cornea of the eye;

an eye-tracking device operable to detect movement of the eye; and a control unit coupled to communicate with said eye diagnostic device, said solid-state laser, said optical scanner, and said eye-tracking device, and operable to control said scanner to produce a customized laser-ablation profile on the cornea for correcting the defect of the eye and to offset said scanner to compensate for any eye movement according to a signal from said eye-tracking device, wherein said solid-state laser comprises a CW optical pumping source, a fundamental solid-state laser, and a wavelength converter, and wherein said wavelength converter includes a fourth harmonic converter.

6. A surgical laser system for customized corneal ablation of a cornea of an eye, comprising:

an eye diagnostic device operable to measure a cornea or refractive defect of the eye;

a solid-state laser operable to produce a pulsed ablation laser beam at a predetermined wavelength, wherein said ablation laser beam is power stabilized and near diffraction-limited;

an optical scanner positioned to receive and scan said ablation laser beam on the cornea of the eye;

an eye-tracking device operable to detect movement of the eye; and a control unit coupled to communicate with said eye diagnostic device, said solid-state laser, said optical scanner, and said eye-tracking device, and operable to control said scanner to produce a customized laser-ablation profile on the cornea for correcting the defect of the eye and to offset said scanner to compensate for any eye movement according to a signal from said eye-tracking device wherein said solid-state laser comprises a CW optical pumping source, a fundamental solid-state laser, and a wavelength converter, and wherein said wavelength converter includes a fifth harmonic converter.

7. The system as in claim 1, wherein said wavelength converter includes an optical parametric oscillator.

8. A surgical laser system for customized corneal ablation of a cornea of an eye, comprising:

an eye diagnostic device operable to measure a cornea or refractive defect of the eye;

a solid-state laser operable to produce a pulsed ablation laser beam at a predetermined wavelength, wherein said ablation laser beam is power stabilized and near diffraction-limited;

an optical scanner positioned to receive and scan said ablation laser beam on the cornea of the eye;

an eye-tracking device operable to detect movement of the eye; and a control unit coupled to communicate with said eye diagnostic device, said solid-state laser, said optical scanner, and said eye-tracking device, and operable to control said scanner to produce a customized laser-ablation profile on the cornea for correcting the defect of the eye and to offset said scanner to compensate for any eye movement according to a signal from said eye-tracking device, wherein said solid-state laser includes a diode-pumped cascade Ti:sapphire laser.

9. A surgical laser system for customized corneal ablation of a cornea of an eye, comprising:

an eye diagnostic device operable to measure a cornea or refractive defect of the eye;

a solid-state laser operable to produce a pulsed ablation laser beam at a predetermined wavelength, wherein said ablation laser beam is power stabilized and near diffraction-limited;

an optical scanner positioned to receive and scan said ablation laser beam on the cornea of the eye;

an eye-tracking device operable to detect movement of the eye; and a control unit coupled to communicate with said eye diagnostic device, said solid-state laser, said optical scanner, and said eye-tracking device, and operable to control said scanner to produce a customized laser-ablation profile on the cornea for correcting the defect of the eye and to offset said scanner to compensate for any eye movement according to a signal from said eye-tracking device, wherein said solid-state laser includes a diode pumped, Q-switched solid-state laser at a wavelength about 1 micron, and wherein said Q-switched solid-state laser includes a laser medium formed of Nd:YLF, Nd:YAG, or Yb:YAG.

10. The system as in claim 1, wherein said ablation laser beam has a pulse-to-pulse fluctuation smaller than 10%, a repetition rate of about 400–1200 Hz, and a beam spot size of about 300–600 microns on the cornea.

11. The system as in claim 1, wherein said ablation laser beam has a wavelength in the deep TJV range near 210 nm.

12. The system as in claim 1, wherein said ablation laser beam has a wavelength in the mid-infrared range near 3 micron.

13. The system as in claim 1, wherein said scanner has a response rate of near or greater than 500 Hz.

14. The system as in claim 1, wherein said eye-tracking device has a response rate near or greater than 250 Hz.

15. A method for customized corneal ablation, comprising:

determining the cornea or refractive defect of an eye;

using a solid-state laser to produce a power stabilized, near diffraction-limited ablation laser beam at a predetermined wavelength, a repetition rate, spot size, and pulse energy;

scanning said laser beam on a cornea of the eye;

detecting movement of the eye;

controlling said scanning of said laser beam to produce a customized laser-ablation profile on the cornea; and further controlling said scanning of said laser beam to compensate for any eye movement.

16. The method as in claim 15, wherein a rate of said scanning is near or greater than 500 Hz, wherein said detecting of the eye movement has a response rate near or greater than 250 Hz, wherein the solid-state laser has a pulse-to-pulse fluctuation smaller than 10%, a repetition rate from about 400 Hz to about 1200 Hz, and a beam spot size from about 300 to about 600 microns on the cornea.

17. A surgical laser system for customized corneal ablation of a cornea of an eye, comprising:

an eye diagnostic device operable to measure a cornea or refractive defect of the eye;

a solid-state laser operable to produce a pulsed ablation laser beam at a laser wavelength that is near diffraction-limited and has a pulse-to-pulse fluctuation smaller than 10%, and a repetition rate from about 400 Hz to about 1200 Hz;

an optical scanner positioned to receive and scan said ablation laser beam on the cornea of the eye at a scanning rate of near or greater than 500 Hz;

an eye-tracking device operable to detect movement of the eye at a response rate near or greater than 250 Hz; and a control unit coupled to communicate with said eye diagnostic device, said solid-state laser, said optical scanner, and said eye-tracking device, and operable to control said scanner to produce a customized laser-ablation profile on the cornea for correcting the defect of the eye and to offset said scanner to compensate for any eye movement according to a signal from said eye-tracking device.

18. The system as in claim 17, wherein said ablation laser beam has a wavelength in the deep UV range near 210nm.

19. The system as in claim 17, wherein said ablation laser beam has a wavelength in the mid-infrared range near 3 micron.

20. The systems as in claim 17, wherein said scanner is spaced from the eye about 20 to 30 cm, and the ablation beam has a beam spot size near or less than 3 mm at said scanner and a beam spot size from 300 to 600 microns.

* * * * *